United States Patent [19]

Beers et al.

[11] 3,962,160

[45] June 8, 1976

[54] NOVEL ORGANOFUNCTIONAL (KETOXIMINO) SILANES AND ROOM TEMPERATURE, VULCANIZABLE COMPOSITIONS CONTAINING THE SAME

[75] Inventors: Melvin D. Beers, Elnora; Abe Berger, Schenectady; Stephen B. Hamilton, Schenectady; Terry G. Selin, Schenectady, all of N.Y.

[73] Assignee: General Electric Company, Waterford, N.Y.

[22] Filed: Dec. 10, 1974

[21] Appl. No.: 531,343

[52] U.S. Cl. ............................ 260/18 S; 260/37 SB; 260/46.5 E; 260/46.5 G; 260/448.2 R; 260/448.2 N; 260/448.2 B
[51] Int. Cl.² ........................................ C08L 91/00
[58] Field of Search ................ 260/46.5 E, 46.5 G, 260/448.2 R, 448.2 N, 448.2 B, 448.8 R, 37 SB, 18 S

[56] References Cited
UNITED STATES PATENTS

| | | | |
|---|---|---|---|
| 3,184,427 | 5/1965 | Russell et al. | 260/46.5 G |
| 3,189,576 | 6/1965 | Sweet | 260/46.5 G |
| 3,398,112 | 8/1968 | Johnson et al. | 260/46.5 G |
| 3,471,434 | 10/1969 | Pande et al. | 260/46.5 G |
| 3,517,001 | 6/1970 | Berger | 260/46.5 E |
| 3,622,529 | 11/1971 | Evans | 260/46.5 E |
| 3,714,089 | 1/1973 | Hamilton et al. | 260/46.5 G |
| 3,734,881 | 5/1973 | Shingledecker | 260/37 SB |
| 3,758,441 | 9/1973 | Nitzsche et al. | 260/46.5 G |
| 3,813,364 | 5/1974 | De Zuba et al. | 260/46.5 E |
| 3,829,529 | 8/1974 | Lengnick | 260/46.5 E |

*Primary Examiner*—Melvyn I. Marquis
*Attorney, Agent, or Firm*—Morgan, Finnegan, Pine, Foley & Lee

[57] ABSTRACT

Novel organofunctional (ketoximino) silanes, such as acetoxyethyl tris(methylethylketoximine)silane, are provided which are useful as crosslinking agents chain-extending agents and chain-terminating agents in room temperature vulcanizable silicone elastomers. The room temperature vulcanizable compositions containing these novel organofunctional tris(ketoximino) silanes, which are stable free flowing fluids in the absence of moisture but cure to the rubbery, solid elastic state upon exposure to moisture, the method of making the same and the cured products thereof are also provided. The present room temperature vulcanizable compositions are particularly well suited for applications in conjunction with concrete (cement) substrates.

38 Claims, No Drawings

NOVEL ORGANOFUNCTIONAL (KETOXIMINO) SILANES AND ROOM TEMPERATURE, VULCANIZABLE COMPOSITIONS CONTAINING THE SAME

BACKGROUND OF THE INVENTION

This invention relates to fluid organopolysiloxanes which are capable of vulcanizing at room temperature upon exposure to moisture to rubbery materials and to organofunctional tris(ketoximino) silane crosslinking agents, chain-extending agents and chain-terminating agents, useful in such compositions.

Generally, prior art room temperature vulcanizable materials (RTV's) comprise a linear polymer and a crosslinking agent.

Some of the prior art crosslinking agents which have commercial success are either solid at room temperature, unstable at room temperature, or both. A disadvantage of the prior art crosslinking agents which are solid at room temperature is that they must be heated to the liquid state prior to use. Crosslinking agents which are unstable at room temperature must be maintained under refrigeration prior to use. Failure to maintain the materials under refrigeration results in disproportionation, and a defective product.

U.S. Pat. No. 3,714,089 to Hamilton et al, incorporated herein by reference, discloses an improved crosslinking agent for room temperature vulcanizing compositions, which are not burdened with the disadvantages of the prior art crosslinking agents. A representative crosslinking agent within the scope of Hamilton et al is acetoxyethyltriacetoxysilane.

Although the room temperature vulcanized compositions of Hamilton et al are particularly well suited for many bonding applications, as a result of the liberation of acetic acid during the curing mechanism, they are not particularly well suited for applications in conjunction with substrates such as concrete, wherein the liberated acetic acid or other deleterious material is corrosive or otherwise detrimental.

SUMMARY OF THE INVENTION

Accordingly, it is one object of the present invention to provide novel crosslinking agents, chain-extending agents and chain-terminating agents useful in room temperature vulcanizable compositions.

Another object of this invention is to provide novel crosslinking agents, chain-extending agents and chain-terminating agents for use in room temperature vulcanizable compositions, which are not burdened by the disadvantages of the prior art, such as instability and the liberation of corrosive by-products.

Still another object of the present invention is to provide improved room temperature vulcanizable RTV compositions utilizing the novel crosslinking agents, chain-extending agents and chain-terminating agents of the present invention, said RTV compositions generally useful for all the same applications as the prior art RTV's, but being particularly well suited in those applications where the liberation of corrosive by-products, such as acetic acid, are deleterious.

These and other objects are accomplished herein by providing organofunctional (ketoximino)silanes characterized by the general formula

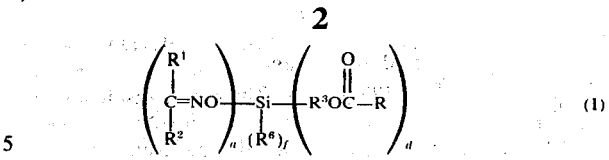

wherein R, $R^1$, $R^2$, $R^3$, $R^6$, a, d, and f are as defined hereinafter, and room temperature vulcanizable organopolysiloxane compositions comprised of a silanol chain-stopped polydiorganosiloxane and at least one of the organofunctional (ketoximino) silanes characterized by formula I hereinabove.

DETAILED DESCRIPTION OF THE INVENTION

The silanol chain-stopped polydiorganosiloxanes useful in the room temperature vulcanizing compositions of this invention are represented by the formula,

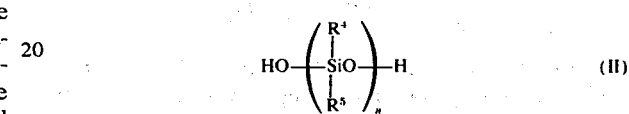

wherein $R^4$ and $R^5$ are each organic radicals of not more than 8 carbon atoms selected from the group consisting of hydrocarbyl, halohydrocarbyl and cyano lower alkyl, and n is a number from about 10 to about 15,000 or more.

The silanol chain-stopped polydiorganosiloxanes are well known in the art and include compositions containing different $R^4$ and $R^5$ groups. For example, the $R^4$ groups can be methyl, while the $R^5$ groups can be phenyl and/or betacyanoethyl. Furthermore, within the scope of the definition of polydiorganosiloxanes useful in this invention are copolymers of various types of diorganosiloxane units, such as silanol chain-stopped copolymers of dimethylsiloxane units, diphenylsiloxane units and methylphenylsiloxane units or, for example, copolymers of dimethylsiloxane units, methylphenylsiloxane units and methylvinylsiloxane units. Preferably, at least 50 percent of the $R^4$ and $R^5$ groups of the silanol chain-stopped polydiorganosiloxanes are methyl groups.

A mixture of various silanol chain-stopped polydiorganosiloxanes also can be employed. The silanol chain-stopped materials useful in the RTV compositions of this invention have been described as polydiorganosiloxanes but such materials can also contain minor amounts, e.g., up to about 20 percent of monoorganosiloxane units such as monoalkylsiloxane units, e.g., monomethylsiloxane units and monophenylsiloxane units. The technology involved in incorporating monoalkylsiloxane units into RTV compositions is disclosed in U.S. Pat. No. 3,382,205 of Beers (1968), which is hereby incorporated into the present case by reference. The silanol chain-stopped materials may also contain triorganosiloxane units, such trialkylsiloxane units, e.g., trimethylsiloxane units, tributylsiloxane units and triphenylsiloxane units. The silanol chain-stopped materials can also contain t-alkoxysiloxane units, e.g., t-butoxy-siloxane units, t-pentoxysiloxane units, and t-amyloxy-siloxane units. Effective results can be obtained if sufficient t-alkoxysiloxane is utilized in combination with the silanol-terminated polydiorganosiloxane of formula (3) to provide a polymer having a ratio of t-alkoxysiloxane units to silanol of 0.05 to 0.9 and preferably 0.2 to 0.8 tertalkoxydialkylsiloxy units per silanol. Many of the t-alkoxysiloxanes useful as part of the silanol chain-stopped materials are described and claimed in U.S. Pat. No. 3,438,930 of Beers, which issued Apr. 15, 1969, the disclosure of which is expressly incorporated herein by reference.

The silanol chain-stopped polydiorganosiloxanes employed in the practice of the present invention can vary from thin fluids to viscous gum, depending upon the value of n and the nature of the particular organic groups represented by $R^4$ and $R^5$.

The novel organofunctional (ketoximino) silane crosslinking agents, chain-extending agents and chain-terminating agents of the present invention are characterized by the general formula I hereinabove, namely,

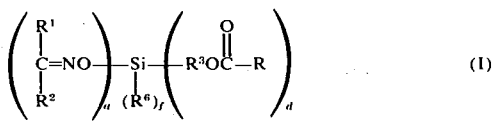

(1)

wherein R is a radical having not more than 8 carbon atoms selected from the group consisting of hydrocarbyl, halo-hydrocarbyl, nitrohydrocarbyl, alkoxyhydrocarbyl, and cyanoalkyl; $R^1$ and $R^2$ may be the same or different and are selected from the group consisting of $C_1$-$C_8$ alkyl and $C_1$-$C_8$ haloalkyl; $R^3$ is at least one divalent radical having from about two to about eight carbon atoms selected from the group consisting of divalent saturated hydrocarbon radicals, halo substituted divalent saturated hydrocarbon radicals, and alkoxy substituted divalent saturated hydrocarbon radicals; $R^6$ is at least one radical selected from the same group as R; $a$ is a number from 1 to 3, $d$ is a number from 1 to 3, $f$ is a number from 0 to 2 and the sum of $a$, $d$ and $f$ is 4.

More specifically, and again referring to Formula I hereinabove, R can be, for example, mononuclear aryl, such as phenyl, benzyl, tolyl, xylyl, and ethylphenyl; halogen-substituted mononuclear aryl, such as 2,6-dichlorophenyl, 4-bromophenyl, 2,5-diphenoxyphenyl, 2,4,6-trichlorophenyl and 2,5-dibromophenyl; nitro-substituted mononuclear aryl, such as 4-nitrophenyl and 2,6-dinitrophenyl; alkoxy-substituted mononuclear aryl, such as 4-methoxyphenyl, 2,6-dimethoxyphenyl, 4-t-butoxyphenyl, 2-ethoxyphenyl, and 2,4,6-trimethoxyphenyl; aralkyl, such as benzyl and halo, nitro and alkoxy derivatives thereof; alkyl such as methyl, ethyl, n-propyl, isopropyl, n-butyl, sec-butyl, isobutyl, tert-butyl, amyl, hexyl, heptyl, octyl, and the various homologs and isomers of alkyl of not more than about eight carbon atoms, alkenyl such as vinyl, allyl, n-butenyl-1, n-butenyl-2, n-pentenyl-2, n-hexenyl-2, 2,3-dimethylbutenyl-2, n-heptenyl, and the various homologs and isomers of alkenyl of not more than about eight carbon atoms, alkynyl such as propargyl, 2-butynyl and the various homologs and isomers of alkynyl of not more than about eight carbon atoms; haloalkyl such as chloromethyl, iodomethyl, bromomethyl, fluoromethyl, chloroethyl, iodethyl, bromoethyl, fluoroethyl, trichloromethyl, diiodoethyl, tribromomethyl, trifluoromethyl, dichloroethyl, chloro-n-propyl, bromo-n-propyl, iodoisopropyl, bromo-n-butyl, bromo-tertbutyl, 1,3,3-trichlorobutyl, 1,3,3-tribromobutyl, chloropentyl, bromopentyl, 2,3-dichloropentyl, 3,3-dibromopentyl, chlorohexyl, bromohexyl, 2,4-dichlorohexyl, 1,3-dibromohexyl, 1,3,4-trichlorohexyl, chloroheptyl, bromoheptyl, fluoroheptyl, 1,3-dichloroheptyl, 1,4,4-trichloroheptyl, 2,4-dichloromethylheptyl, chlorooctyl, bromooctyl, iodooctyl, 2,4-dichoromethylhexyl, 2,4-dichlorooctyl, 2,4,4-trichloromethylpentyl, 1,3,5-tribromooctyl and the various homologs and isomers of haloalkyl of not more than about eight carbon atoms; haloalkenyl such as chlorovinyl, bromovinyl, chloroallyl, bromoallyl, 3-chloro-n-butenyl-1, 3-chloro-n-pentenyl-1, 3-fluoro-n-heptenyl-1, 1,3,3-trichloro-n-heptenyl-5, 1,3,5-trichloro-n-octenyl-6, 2,3,3-trichloromethylpentenyl-4 and the various homologs and isomers of haloalkenyl of not more than about eight carbon atoms, haloalkynyl such as chloropropargyl, bromopropargyl and the various homologs and isomers of haloalkynyl of not more than about eight carbon atoms; nitroalkyl such as nitromethyl, nitroethyl, nitro-n-propyl, nitro-n-butyl, nitropentyl, 1,3-dinitroheptyl and the homologs and isomers of nitroalkyl of not more than about eight carbon atoms; nitroalkenyl such as nitroallyl, 3-nitro-n-butenyl-1, 3-nitro-n-heptenyl-1, and the various homologs and isomers of nitroalkenyl of not more than about eight carbon atoms; nitroalkynyl such as nitropropargyl and the various homologs and isomers of nitroalkynyl of not more than about 8 carbon atoms; alkoxyalkyl and polyalkoxyalkyl such as methoxymethyl, ethoxymethyl, butoxymethyl, methoxyethyl, ethoxyethyl, ethoxyethoxyethyl, methoxyethoxymethyl, butoxymethoxyethyl, ethoxybutoxyethyl, methoxypropyl, butoxypropyl, methoxybutyl, butoxybutyl, methoxypentyl, butoxypentyl, methoxymethoxypentyl, butoxyhexyl, methoxyheptyl and the various homologs and isomers of alkoxyalkyl and polyalkoxyalkyl of not more than about eight carbon atoms; alkoxyalkenyl and polyalkoxyalkenyl such as ethoxyvinyl, methoxyallyl, butoxyallyl, methoxy-n-butenyl-1, butoxy-n-pentenyl-1, methoxyethoxy-n-heptenyl-1, and the various homologs and isomers of alkoxyalkenyl and polyalkoxyalkenyl of not more than about 8 carbon atoms, alkoxyalkynyl and polyalkoxy-alkynyl such as methoxypropargyl and the various homologs and isomers of alkoxyalkynyl and polyalkoxyalkynyl of not more than about eight carbon atoms; cycloalkyl, cycloalkenyl and alkyl, halogen, alkoxy and nitro-substituted cycloalkyl and cycloalkenyl such as cyclopentyl, cyclohexyl, cycloheptyl, cyclooctyl, 6-methylcyclohexyl, 3,4-dichlorohexyl, 2,6-dibromocycloheptyl, 6-methoxycyclooctyl, 2-nitrocyclopentyl, 1-cyclopentenyl, 3-methyl-1-cyclopentenyl, 5-methoxy-1-cyclopentenyl, 5-methyl-5-cyclopentenyl, 3-4-dichloro-5-cyclopentenyl, 5-(tert-butyl)-1-cyclopentenyl, 2-nitro-1-cyclohexenyl, 1-cyclohexenyl, 3-methyl-1-cyclohexenyl, 3,4-dimethyl-1-cyclohexenyl and 6-methoxy-1-cyclohexenyl; and cyano lower alkyl such as cyanomethyl, beta-cyanoethyl, gamma-cyanopropyl, delta-cyanobutyl, and gamma-cyanoisobutyl.

Included among the $R^1$ and $R^2$ radicals, which can be the same or different, are, for example, methyl, ethyl, propyl, butyl, isobutyl, pentyl, etc.; chloroethyl, 1-bromobutyl, 2-fluoropentyl and the like.

As stated hereinabove, $R^6$ is the same as R.

Included among the $R^3$ radicals are, for example,

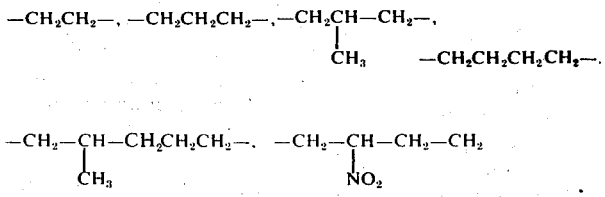

and

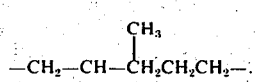

The organofunctional (ketoximino) silanes of the present invention represented by Formula I hereinabove are prepared by the following general procedure. The first step of the procedure involves reacting a silane with an olefinically unsaturated ester via the following SiH-olefin addition reaction to produce the following composition:

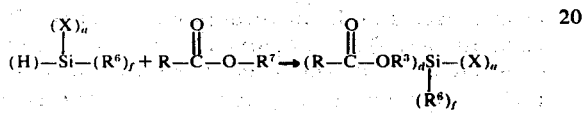

wherein R, $R^3$, $R^6$, a, b, d and f are as defined above, $R^7$ is an unsaturated radical having from about two to about eight carbon atoms selected from the group consisting of olefinically unsaturated hydrocarbon radicals and halo, nitro, and alkoxy-substituted olefinically unsaturated hydrocarbon radicals, and X is a halogen selected from the group consisting of F, Cl, Br, and I. The reaction is catalyzed by a platinum compound or platinum complex catalyst. Both the platinum compound catalysts and the platinum complex catalysts are well known in the art and are described, among other places, in U.S. Pat. Nos. 2,823,218 — Speier, 3,159,601 — Ashby, 3,159,662 — Ashby, and 3,220,972 — Lamoreaux.

Examples of compounds of the formula

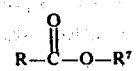

above, which can be used in the above reaction include the following:

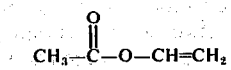

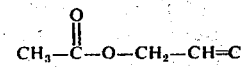

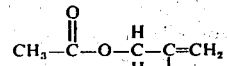

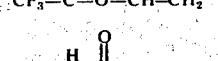

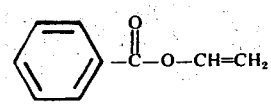

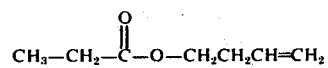

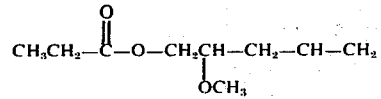

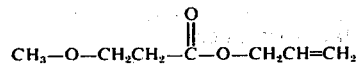

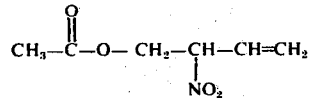

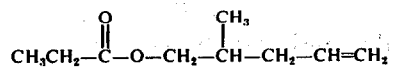

The next step in preparing the novel crosslinking agents, chain-extending agents and chain-terminating agents of this invention involves reacting the SiH-olefin addition product of the first step described above with an organofunctional ketoxime having the formula

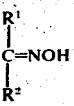

in the presence of a tertiary amine base. Using, for example, triethylamine as the base, this step is shown as follows:

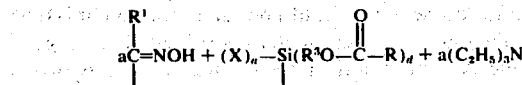

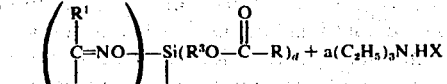

wherein $R^1$, $R^2$, $R^3$, $R^6$, X, a, d and f are as defined above and all a's are the same.

This second reaction step shown above is generally carried out at room to reflux temperature and atmospheric pressure in the presence of a solvent, such as ether and is generally completed in about 2 to 6 hours.

The product is removed from the reaction mixture by filtering off the solid precipitate of amine hydrohalogen and stripping the solvent.

Included among the

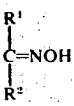

ketoximes used herein are, for example, methyl ethyl ketoxime, i.e.,

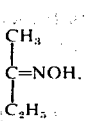

diethyl ketoxime, i.e.,

methyl propylketoxime, i.e.,

chloromethyl ethyl ketoxime, i.e.

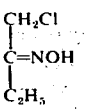

and the like.

The room temperature vulcanizable compositions of the present invention are prepared by simply admixing one or more of the organofunctional (ketoximino) silanes represented by Formula I above with the silanol chain-stopped polydiorganosiloxanes represented by Formula II above. The components are preferably at room temperature during mixing. Since the silanes tend to hydrolyze upon contact with moisture, care should be exercised to exclude moisture during the addition of the silane to the silanol chain-stopped polydiorganosiloxane. Likewise, care should be taken that the mixture of the silane and the silanol chain-stopped polydiorganosiloxane is maintained under substantially anhydrous conditions if it is desired to store the admixture for an extended period of time prior to conversion of the composition to the cured, solid, elastic silicone rubber state. On the other hand, if it is desired to permit the mixture to cure immediately upon admixture of the silane and the polydiorganosiloxane, no special precautions are necessary and the two components can be mixed and placed in the form or shape in which it is desired for the composition to be cured.

The amount of the silane admixed with the silanol chain-stopped polydiorganosiloxane can vary within wide limits. However, for best results, it is preferred to add an excess of one mole of the silane per mole of silanol groups in the silanol chain-stopped polydiorganosiloxanes. Satisfactory curing can be obtained, for example, with from 1.0 to 4 moles of the silane per mole of silanol groups in the polydiorganosiloxane. No particular benefit is derived from using more than 4 moles of the silane per mole of the polydiorganosiloxane. The temperature at which the silane and the silanol chain-stopped polydiorganosiloxane are admixed is not critical and a room temperature addition is usually employed.

The admixture can be carried out in the presence of an inert solvent (that is a solvent which will not react with the ketoximino, silanol, alkoxy or acyloxy groups on the silicon). Suitable solvents include hydrocarbons such as benzene, toluene, xylene or petroleum ethers, halogenated solvents such as perchloroethylene or chlorobenzene and organic ethers such as diethylether and dibutylether; ketones such as methylisobutylketone and fluid hydroxyl-free polysiloxanes.

The presence of a solvent is particularly advantageous when the silanol chain-stopped polydiorganosiloxane is a high molecular weight gum. The solvent reduces the overall viscosity of the composition and facilitates cure. The RTV compositions may be kept in the solvent until they are to be used. This is particularly valuable when a gummy composition is to be employed in coating applications.

The RTV compositions of this invention are stable in the absence of moisture. Consequently, they can be stored for prolonged periods of time without deleterious effect. During this period of storage no significant change occurs in the physical properties of the RTV compositions. This is of particular importance from a commercial standpoint, since it assures that once an RTV composition is prepared with a certain consistency and cure time that neither will change significantly upon storage. Storage stability is one of the characteristics which makes the compositions of this invention particularly valuable as a one component room temperature vulcanizing composition.

A wide choice of components is available in the preparation of the RTV compositions of the present invention. In general, the particular components employed are a function of the properties desired in the cured silicone rubber. Thus, with a particular silane, some variation in the properties of the cured silicone rubber are obtained by varying the molecular weight (as measured by viscosity) of the silanol chain-stopped polydiorganosiloxane. For a given system, as the viscosity of the silanol chain-stopped starting material increases, the hardness of the cured rubber decreases while the elongation increases. On the other hand, with a lower viscosity material, the cure is tighter so that the cured rubber has a lower elongation and increased hardness.

RTV compositions prepared by mixing the silane with the silanol chain-stopped polydiorganosiloxanes can be used without further modification in many sealing, caulking or coating applications by merely placing the compositions in the desired place and permitting them to cure upon exposure to the moisture present in the atmosphere. Upon exposure of such compositions to atmospheric moisture, even after storage for times as long as 2 years or more, a "skin" will form on the compositions shortly after exposure and cure to the rubbery state will occur within 12 to 24 hours, all at room temperature. The time required for the formation of such skin can vary from a minimum of about 5 to 10 minutes to a maximum of about 1 hour.

It is often desirable to modify the RTV compositions of the present invention by the addition of various materials which act as extenders or which change various properties such as cure rate and color. For example, if it is desired to reduce the time required for complete cure, the composition can be modified by the incorporation of a minor amount of carboxylic acid salt and/or chelates of a metal ranging from lead to manganese, inclusive, in the electromotive series of metals. The particular metals included are lead, tin, nickel, cobalt, iron, cadmium, chromium, zinc and manganese. The carboxylic acids from which the salts of these metals are derived can be monocarboxylic acids or dicarboxylic acids and the metallic salts can be either soluble or insoluble in the silanol chain-stopped polydiorganosiloxane. Preferably, the salts employed are soluble in the silanol chain-stopped polydiorganosiloxane since this facilitates the uniform dispersion of the salt in the reaction mixture.

Illustrative of metal salts which can be employed are, for example, zinc naphthenate, lead naphthenate, cobalt naphthenate, iron 2-ethylhexoate, cobalt octoate, zinc octoate, chromium octoate and tin octoate. Operative metal salts include those in which the metallic ion contains a hydrocarbon substituent such as, for example, carbomethoxyphenyl tin tris-uberate, isobutyl tin triceroate, cyclohexenyl lead triactotinate, xenyl lead tris-alicylate, dimethyl tin dibutyrate, basic dimethyl tin oleate, dibutyl tin diacetate, dibutyl tin dilaurate, divinyl tin diacetate, dibutyl tin dibenzoate, dibutyl tin dioctoate, dibutyl tin maleate, dibutyl tin adipate, diisoamyl tin bis-trichloro benzoate, diphenyl lead diformate, dibutyl tin dilacetate, dicyclopentyl lead bis-monochloroacetate, dibenzyl lead di-2-pentanoate, diallyl lead di-2-hexenoate, triethyl tin tartrate, tributyl tin acetate, triphenyl tin acetate, tricyclohexyl tin acrylate, tritolyl tin terephthalate, tri-n-propyl lead acetate, tristearyl lead succinate, trinaphthyl lead p-methylbenzoate, tris-phenyl lead cyclohexenyl acetate, triphenyl lead ethylmalonate, etc.

The amount of the metal salt of the organic carboxylic acid which can be employed is a function of the increased rate of curing desired so that any amount for increasing the cure rate can be employed. In general, no particular benefit is derived from employing more than about 5 percent by weight of such metal salt based on the weight of the silanol chain-stopped polydiorganosiloxane. Preferably, where such metal salt is employed, it is present in an amount equal to from about 0.01 to 2.0 percent by weight, based on the weight of the polydiorganosiloxane.

Metal chelates such as those disclosed in U.S. Pat. Nos. 3,334,067 and 3,065,194 can also be used in the RTV compositions of this invention as catalysts in amounts from 0.01 part to about 10 parts based on 100 parts of the silanol chain-stopped polydiorganosiloxane.

The RTV compositions of the present invention can also be varied by the incorporation of various extenders or fillers. Illustrative of the many fillers which can be employed with the compositions of the present invention are titanium dioxide, lithopone, zinc oxide, zirconium silicate, silica aerogel, iron oxide, diatomaceous earth, calcium carbonate, fumed silica, silazane treated silica, precipitated silica, glass fibers, magnesium oxide, chromic oxide, zirconium oxide, aluminum oxide, crushed quartz, calcined clay, asbestos, carbon, graphite, cork, cotton, synethetic fibers, etc. Silazane treated silica fillers such as those disclosed and claimed in application Ser. No. 789,352 of Smith filed Jan. 6, 1969 now U.S. Pat. No. 3,635,743, and particularly suitable for use in the RTV compositions of the present invention, they are generally employed in amounts from about 5 to about 200 parts filler, per 100 parts of silanol chain-stopped polydiorganosiloxane.

In addition to the modification of the RTV compositions of the present invention by addition of metal salt, cure accelerators and fillers, these compositions can also be modified by the incorporation of various flame retardants, stabilizing agents and plasticizers such as siloxane fluids. Suitable flame retardants include antimony oxide, various polychlorinated hydrocarbons and organic sulfonates.

Where the compositions of the present invention contain components other than the silane and the polydiorganosiloxane, the various ingredients can be added in any desired order. However, for ease of manufacturing it is often convenient to form a blend or mixture of all of the components of the room temperature vulcanizing organopolysiloxane except the silane, to then remove moisture from the resulting mixture by maintaining the mixture under vacuum and thereafter to add the silane prior to packaging the composition in containers protected from moisture.

The preferred silanol chain-stopped polydiorganosiloxane to be used in combination with the novel organofunctional (ketoximino) silane crosslinking agents of the invention are silanol chain-stopped polydiorganosiloxanes having a viscosity in the range of from about 100 centipoises to about 120,000 centiposes at 25°C. The preferred polydiorganosiloxanes are polydimethylsiloxanes having from about 10 to about 15,000 dimethylsiloxy units per molecule and can contain some t-butoxy groups.

Generally speaking, in the preferred embodiment of the present invention, at least 50 percent of the groups represented by $R^4$ and $R^5$ in formula II above are methyl radicals, remainder phenyl, and n is a number from 10 to 15,000.

In the preferred embodiments regarding Formula I above, R is a radical of not more than 4 carbon atoms, most preferably, methyl, $R^1$ and $R^2$ are radicals of not more than 3 carbon atoms, $R^3$ is an alkylene radical of not more than 4 carbon atoms, most preferably 2 carbon atoms, and $R^6$ is the same as R.

When the silane of Formula I is employed as a cross-linking agent, a has a value of 3. When it is desired to have a chain-extending agent employed in combination with the cross-linking agent, a has a value of 2 resulting in the silane being difunctional. The presence of a chain-extending agent results in a final cured product having a higher degree of elasticity. The same result would be obtained if a higher molecular weight silanol-stopped fluid were used; however, the use of such a high molecular weight silanol-stopped fluid would result in a much higher viscosity of the curable composition resulting in difficulties in handling the extremely viscous material. When it is desired to improve the modulus of elasticity, a silane of Formula I, wherein a has a value of 1, is incorporated into the RTV composition. The use of this monofunctional silane chain terminating unit in combination with the cross-linking and optionally chain-extending silanes discussed above, not only results in a higher modulus of elasticity but in many instances also improves the adhesion of the cured composition to a substrate.

The preferred organofunctional (ketoximino) silanes within the scope of Formula I above used in the room temperature vulcanizable compositions described in the present invention contain on the average from 2.05 to 3 silicon-bonded ketoximino groups, i.e.,

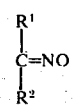

per silane when a fluid containing two silanol end stoppers is used. Average in this situation means the total number of silicon bonded ketoximino radicals divided by the total number of silane molecules used in the room temperature vulcanizable composition.

The most preferred organofunctional (ketoximino) silane within the scope of Formula I above is tris(methylethyl ketoximino) silylethyl acetate, also called acetoxyethyl tris(methylethylketoximino) silane represented by the formula

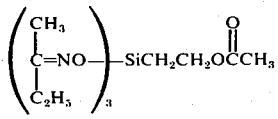

The preferred RTV compositions of the present invention include a tin catalyst such as dibutyltindilaurate or tin octoate. For deep section cure and some other curing needs the preferred catalyst is basic dimethyltinoleate.

The preferred RTV compositions of the present invention also include fillers, the most preferred of which is the silazane treated silica filler disclosed and claimed in application Ser. No. 789,352 of Smith, filed Jan. 6, 1969 now U.S. Pat. No. 3,635,743. The fillers are preferably used in amounts from about 10 to about 100 parts of filler, per 100 parts of the silanol chain-stopped polydiorganosiloxane.

The silazane treated filler can be prepared by the following procedure. A fumed silica filler is contacted with ammonia for about 1½ hours at 25°C with agitation. Hexamethyldisilazane is added to the treated filler in an amount of about 20 parts per 100 parts of treated filler and the mixture is heated to about 130°C for about 2 hours. Water in an amount of about one part by weight is added to the mixture and heating is continued at 130°C for an additional hour. The treated silica filler is then purged with $N_2$ at 130°C until the $NH_3$ content is 50 ppm.

The room temperature vulcanizable compositions of the present invention are generally useful for those applications for which compositions of this type have become known. Such applications include, for example, caulking and sealing, whether household or industrial such as in buildings, factories, automotive equipment and in applications where adhesion to masonry, glass, plastic, metal and wood is required. As stated hereinabove, the present room temperature compositions, as a result of the use therein of the present organofunctional (ketoximino) silane crosslinkers, are particularly well suited for applications with concrete substrates since corrosive materials, such as acetic acid, are not liberated during the curing mechanism, as is the case with prior art compositions.

In order that those skilled in the art may better understand how the present invention may be practiced, the following examples are given by way of illustration, and not by way of limitation.

EXAMPLE 1

This example illustrates the preparation of tris(methylethylketoximino) silylethyl acetate according to this invention.

Into a reaction flask containing 261.3 grams of methylethylketoxime (3 moles), 313 grams of triethyl amine (3.1 moles) and 1000 mls. of anhydrous diethyl ether, and well protected from atmospheric moisture by a dry nitrogen purge, is added dropwise with efficient stirring 221.5 grams of acetoxyethyltrichlorosilane. (The acetoxyethyltrichlorosilane is prepared according to the well-known reaction of vinyl acetate and trichlorosilane.) An exothermic reaction occurs as the ether begins to reflux gently after about 5–10% of the silane addition, a white precipitate of triethylamine hydrochloride is formed. As the reaction progresses, an additional 500 ml. of ether is added to maintain a fluid mixture. After the addition of the silane is complete, the reaction mixture is kept at reflux (with the assistance of external heat) for 4 additional hours. The reaction mixture is cooled, carefully filtered and the ether is stripped.

Infrared analysis shows a broad ≡ Si-O-N=band in the region $10.5\mu$ to $11\mu$, =C=N-absorption at the 6.1 and =C=O band at $5.76\mu$, confirming the structure

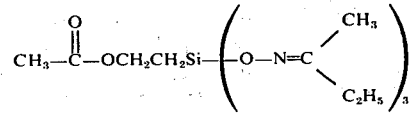

Chloride analysis indicates a level below 5 ppm.

EXAMPLE 2

This example illustrates the preparation of a room temperature vulcanizable composition employing the silane compound prepared in Example 1 as a crosslinking agent and the cured product thereof.

100 parts by weight of a base compound is mixed at room temperature with 4 parts by weight of acetoxyethyl tris(methylethylketoximino) silane crosslinking agent prepared in Example 1, and 0.10 parts by weight of a basic dimethyltin oleate catalyst. The base compound consists of 100 parts by weight of a silanol terminated polydimethylsiloxane fluid having a viscosity of 7000 centipoise at 25°C, 20 parts by weight of an octamethylcyclotetrasiloxane treated fumed silica having a surface area of approximately 200 square meters per gram, 1.8 parts by weight of titanium dioxide, and 7.0 parts by weight of a process aid which is prepared according to U.S. Pat. No. 3,382,205. The process aid consists of 7 mole percent of monomethylsiloxy units, 73 mole percent of dimethylsiloxy units, 20 mole percent of trimethylsiloxy units and contains 0.5 weight percent silanol. The process aid has a viscosity of 30 centipoise at 25°C and is devolatilized.

The resultant room temperature vulcanizable composition gives a tack-free surface in 10 minutes when it is exposed to moisture and is cured through a ⅛ inch thickness in approximately 5 hours to a tough elastomeric rubber.

EXAMPLE 3

This example illustrates the preparation of another room temperature vulcanizable composition using the silane compound prepared in Example 1 and the cured product thereof.

100 parts by weight of a base compound is mixed at room temperature with 6 parts by weight of acetoxyethyl tris(methylethylketoximino) silane, prepared according to Example 1, and 0.066 parts by weight of dibutyltin dilaurate catalyst. The base compound consists of 100 parts by weight of a silanol terminated polydimethylsiloxane fluid having a viscosity of 3,000 centipoise at 25°C, 4.0 parts by weight of a trimethylsilyl terminated oil having a viscosity of 21 centistokes at 25°C and a composition of about 25 mole percent of diphenylsiloxy groups and 75 mole percent dimethylsiloxy groups (acts as a thixotrope), 17.0 parts by weight of octamethylcyclotetrasiloxane treated fumed silica having a surface area of about 200 m²/g, 3.0 parts by weight titanium dioxide and 5.0 parts by weight of the process aid used in Example 2.

After curing at room temperature for 72 hours the following physical properties are observed:

| | |
|---|---|
| shore A hardness | 36 |
| tensile strength, psi | 450 |
| elongation, % | 350 |
| tack free time | 1¼ hrs. |
| application rate, g/min (⅛ in. orifice at 90 psi pressure) | 550 |

EXAMPLE 4

This example illustrates the preparation of still another room temperature vulcanizable composition and cured product thereof of the present invention.

100 parts by weight of a base compound is mixed at room temperature with 6.0 parts by weight of acetoxyethyl tris(methylethylketoximino) silane prepared according to Example 1, and 0.06 parts by weight of dibutyltin dilaurate catalyst. The base compound consists of 100 parts by weight of a silanol terminated polydimethylsiloxane fluid having a viscosity of about 5,000 centipoise at 25°C and 20 parts by weight of hexamethyldisilazane treated fumed silica having a surface area of about 200 m²/g. The cured product has the following properties:

| | |
|---|---|
| shore A hardness | 35 |
| tensile strength, psi | 500 |
| elongation, % | 450 |
| tack free tim | ¾ hr. |

Obviously, other modifications and variations of the present invention are possible in the light of the above teachings.

For example, in order to improve the adhesiveness of the present room temperature vulcanizable compositions, adhesion promotors, such as 1,3,5-gamma tris-trimethoxysilylpropylisocyanurate, 1,3,5-gamma tris-methyldimethoxysilylpropylisocyanurate, and 1,3,5-gamma tris-dimethylmethoxypropylisocyanurate may be added thereto.

It is therefore to be understood that changes may be made in the particular embodiments of this invention which are within the full intended scope of the invention as defined by the appended claims.

What is claimed and desired to be secured by Letters Patent of the United States is:

1. A compound having the general formula,

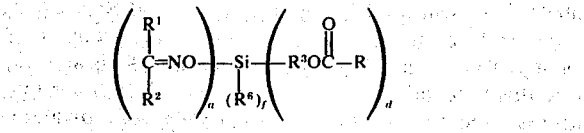

wherein R is a radical having not more than about 8 carbon atoms and is selected from the group consisting of hydrocarbyl, halohydrocarbyl, nitrohydrocarbyl, alkoxyhydrocarbyl and cyanoalkyl, $R^1$ and $R^2$ are the same or different and are selected from the group consisting of $C_1$-$C_8$ alkyl and $C_1$-$C_8$ haloalkyl, $R^3$ is at least one divalent radical having from about 2 to 8 carbon atoms selected from the group consisting of a divalent saturated hydrocarbon, a halogen substituted divalent saturated hydrocarbon and an alkoxy substituted divalent saturated hydrocarbon, $R^6$ is at least one radical selected from the same group as R, $a$ is a number from 1 to 3, $d$ is a number from 1 to 3, $f$ is a number from 0 to 2 and the sum of $a$, $d$ and $f$ is 4.

2. A compound according to claim 1 wherein R is a radical having not more than 8 carbon atoms and is selected from the group consisting of mononuclear aryl, halo-substituted mononuclear aryl, nitro-substituted mononuclear aryl, alkoxy-substituted mononuclear aryl, aralkyl, halo-substituted aralkyl, nitro-substituted aralkyl, alkoxy-substituted aralkyl, alkyl, halo-subsituted alkyl, nitro-substituted alkyl, alkoxy-substituted alkyl, cyanoalkyl, cycloalkyl, halo-substituted cycloalkyl, nitro-substituted cycloalkyl, alkoxy-substituted cycloalkyl, alkenyl, halo-substituted alkenyl, nitro-substituted alkenyl, alkoxy-substituted alkenyl, alkynyl, halo-substituted alkynyl, nitro-substituted alkynyl, and alkoxy-substituted alkynyl.

3. A compound according to claim 2 wherein R, $R^1$, $R^2$, and $R^6$ are the same or different alkyl radicals, and $R^3$ is a divalent saturated hydrocarbon radical.

4. A compound according to claim 2 wherein R, $R^1$, $R^2$, and $R^6$ are the same or different alkyl, $R^3$ is a divalent saturated hydrocarbon radical and $f$ is 1, $a$ is 2 and $d$ is 1.

5. A compound according to claim 2 wherein R, $R^1$ and $R^2$ are the same or different alkyl, $R^3$ is a divalent saturated hydrocarbon radical, $f$ is 0, $a$ is 2 and $d$ is 2.

6. A compound according to claim 2 wherein R, $R^1$ and $R^2$ are the same or different alkyl, $R^3$ is a divalent saturated hydrocarbon radical, $f$ is 0, $a$ is 3 and $d$ is 1.

7. A compound according to claim 2 represented by the formula

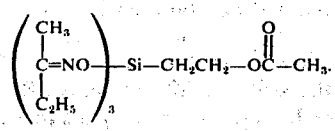

8. A room temperature vulcanizable fluid composition stable under substantially anhydrous conditions and curable to an elastic solid in the presence of moisture which comprises a silanol chain-stopped polydiorganosiloxane represented by the general formula,

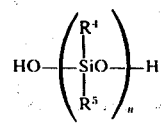

wherein $R^4$ and $R^5$ are each at least one radical having not more than 8 carbon atoms selected from the group consisting of hydrocarbyl, halohydrocarbyl, and cyanoalkyl which radicals may be the same or different, and $n$ is a number from about 10 to about 15,000, and at least one silane represented by the formula,

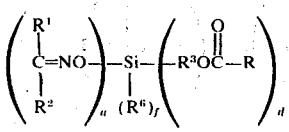

wherein R is a radical having not more than about 8 carbon atoms and is selected from the group consisting of hydrocarbyl, halohydrocarbyl, nitrohydrocarbyl, alkoxyhydrocarbyl, and cyanoalkyl, $R^1$ and $R^2$ are the same or different and are selected from the group consisting of $C_1$–$C_8$ alkyl and $C_1$–$C_8$ haloalkyl, $R^3$ is at least one divalent radical having from about 2 to 8 carbon atoms selected from the group consisting of a divalent saturated hydrocarbon, a halogen substituted divalent saturated hydrocarbon and an alkoxy substituted divalent saturated hydrocarbon, $R^6$ is at least one radical selected from the same group as R, $a$ is a number from 1 to 3, $d$ is a number from 1 to 3, $f$ is a number from 0 to 2 and the sum of $a$, $d$ and $f$ is 4.

9. A composition according to claim 8 wherein at least 50 percent of the total number of $R^4$ and $R^5$ radicals are methyl.

10. The composition of claim 8 wherein at least 50 percent of the total number of $R^4$ and $R^5$ radicals are methyl and the remainder are phenyl.

11. A composition according to claim 8 wherein R is a radical having not more than 8 carbon atoms and is selected from the group consisting of mononuclear aryl, halo-substituted mononuclear aryl, nitro-substituted mononuclear aryl, alkoxy-substituted mononuclear aryl, aralkyl, halo-substituted aralkyl, nitro-substituted aralkyl, alkoxy-substituted aralkyl, alkyl, halo-substituted alkyl, nitro-substituted alkyl, alkoxy-substituted alkyl, cyanoalkyl, cycloalkyl, halo-substituted cycloalkyl, nitro-substituted cycloalkyl, alkoxy-substituted cycloalkyl, alkenyl, halo-substituted alkenyl, nitro-substituted alkenyl, alkoxy-substituted alkenyl, alkynyl, halo-substituted alkynyl, nitro-substituted alkynyl, and alkoxy-substituted alkynyl.

12. A composition according to claim 11 wherein R, $R^1$, $R^2$ and $R^6$ are the same or different alkyl radicals, and $R^3$ is a divalent saturated hydrocarbon.

13. A composition according to claim 11 wherein R, $R^1$, $R^2$ and $R^6$ are the same or different alkyl, $R^3$ is a divalent saturated hydrocarbon radical and $f$ is 1, $a$ is 2 and $d$ is 1.

14. A composition according to claim 11 wherein R, $R^1$ and $R^2$ are the same or different alkyl, $R^3$ is a divalent saturated hydrocarbon radical, $f$ is 0, $a$ is 2 and $d$ is 2.

15. A composition according to claim 11 wherein R, $R^1$ and $R^2$ are the same or different alkyl, $R^3$ is a divalent saturated hydrocarbon radical, $f$ is 0, $a$ is 3 and $d$ is 1.

16. A composition according to claim 11 wherein said silane is represented by the formula,

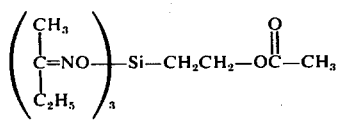

17. A composition according to claim 11 comprised of a silane having the formula

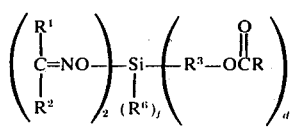

wherein R, $R^1$, $R^2$, $R^3$ and $R^6$ are as defined in claim 11, $f$ is an integer from 0 to 1 and $d$ is an integer from 1 to 2, mixed with a silane having the formula,

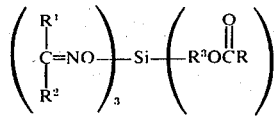

wherein R, $R^1$, $R^2$, and $R^3$, are as defined in claim 11.

18. A composition according to claim 11 being further characterized by having a filler present.

19. A composition according to claim 11 further characterized by having a filler and a curing catalyst present.

20. A composition according to claim 19 wherein said catalyst is selected from the group consisting of a carboxylic acid salt and a carboxylic acid chelate of a metal ranging from lead to manganese, inclusive, in the electromotive series of metals.

21. A composition according to claim 20 wherein the catalyst is basic dimethyltinoleate or dibutyltindilaurate.

22. A composition according to claim 11 being further characterized by having an adhesion promotor present.

23. A composition according to claim 11 when cured to an elastic solid.

24. A method of forming a room temperature vulcanizable fluid composition stable under substantially anhydrous conditions and curable to an elastic solid in the presence of moisture which comprises mixing in the substantial absence of moisture, a silanol chain-stopped polydiorganosiloxane represented by the general formula

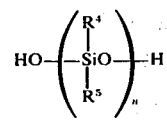

wherein $R^4$ and $R^5$ are each at least one radical having not more than 8 carbon atoms selected from the group consisting of hydrocarbyl, halohydrocarbyl, and cyanoalkyl which radicals may be the same or different, and $n$ is a number from about 10 to about 15,000, and at least one silane represented by the formula,

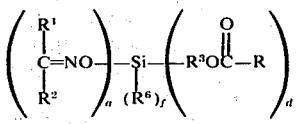

wherein R is a radical having not more than about 8 carbon atoms and is selected from the group consisting of hydrocarbyl, halohydrocarbyl, nitrohydrocarbyl, alkoxyhydrocarbyl, and cyanoalkyl, $R^1$ and $R^2$ are the same or different and are selected from the group consisting of $C_1$–$C_8$ alkyl and $C_1$–$C_8$ haloalkyl, $R^3$ is at least one divalent radical having from about 2 to 8 carbon atoms selected from the group consisting of a divalent saturated hydrocarbon, a halogen substituted divalent saturated hydrocarbon and an alkoxy substituted divalent saturated hydrocarbon, $R^6$ is at least one radical selected from the same group as R, $a$ is a number from 1 to 3, $d$ is a number from 1 to 3, $f$ is a number from 0 to 2 and the sum of $a$, $d$ and $f$ is 4.

25. A method according to claim 24 wherein at least 50% of the total number of $R^4$ and $R^5$ radicals are methyl.

26. A method according to claim 24 wherein at least 50% of the total number of $R^4$ and $R^5$ radicals are methyl and the remainder are phenyl.

27. A method according to claim 24 wherein R is a radical having not more than 8 carbon atoms and is selected from the group consisting of mononuclear aryl, halo-substituted mononuclear aryl, nitro-substituted mononuclear aryl, alkoxy substituted mononuclear aryl, aralkyl, halo-substituted aralkyl, nitro-substituted aralkyl, alkoxy-substituted aralkyl, alkyl, halo-substituted alkyl, nitro-substituted alkyl, alkoxy-substituted alkyl, cyanoalkyl, cycloalkyl, halo-substituted cycloalkyl, nitro-substituted cycloalkyl, alkoxy-substituted cycloalkyl, alkenyl, halo-substituted alkenyl, nitro-substituted alkenyl, alkoxy-substituted alkenyl, alkynyl, halo-substituted alkynyl, nitro-substituted alkynyl, and alkoxy-substituted alkynyl.

28. A method according to claim 27 wherein R, $R^1$, $R^2$ and $R^6$ are the same or different alkyl radicals, and $R^3$ is a divalent saturated hydrocarbon.

29. A method according to claim 27 wherein R, $R^1$, $R^2$ and $R^6$ are the same or different alkyl, $R^3$ is a divalent saturated hydrocarbon radical and $f$ is 1, $a$ is 2 and $d$ is 1.

30. A method according to claim 27 wherein R, $R^1$ and $R^2$ are the same or different alkyl, $R^3$ is a divalent saturated hydrocarbon radical, $f$ is 0, $a$ is 2 and $d$ is 2.

31. A method according to claim 27 wherein R, $R^1$ and $R^2$ are the same or different alkyl, $R^3$ is a divalent saturated hydrocarbon radical, $f$ is 0, $a$ is 3 and $d$ is 1.

32. A method according to claim 27 wherein said silane is represented by the formula,

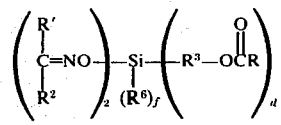

33. A method according to claim 27 wherein a silane having the formula

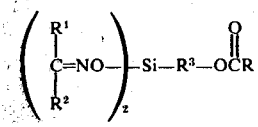

wherein R, $R^1$, $R^2$, $R^3$ and $R^6$ are defined in claim 11, $f$ is an integer from 0 to 1 and $d$ is an integer from 1 to 2 is mixed with a silane having the formula, $$\left( \underset{R^2}{\overset{R^1}{\underset{|}{C}}}=NO \right)_{\!z} \!\!-Si-R^3-O\overset{O}{\overset{\|}{C}}R$$

wherein R, $R^1$, $R^2$, $R^6$ are as defined in claim 11.

34. A method according to claim 27 being further characterized by the admixture of a filler.

35. A method according to claim 11 further characterized by the admixture of a filler and a curing catalyst.

36. A method according to claim 35 wherein said catalyst is selected from the group consisting of a carboxylic acid salt and a carboxylic acid chelate of a metal ranging from lead to manganese, inclusive, in the electromotive series of metals.

37. A method according to claim 36 wherein the catalyst is basic dimethyltinoleate.

38. A method according to claim 27 being further characterized by the admixture of an adhesion promotor.

* * * * *